United States Patent [19]

Greve et al.

[11] Patent Number: 5,801,199
[45] Date of Patent: Sep. 1, 1998

[54] PHARMACEUTICAL COMPOSITION FOR TREATING ACUTE RHINITIS

[75] Inventors: Rainer Greve, Bad Segeberg; Harald Greve, Düsseldorf, both of Germany

[73] Assignee: Maria Clementine Martin, Germany

[21] Appl. No.: 745,291

[22] Filed: Nov. 8, 1996

[30] Foreign Application Priority Data

Nov. 10, 1995 [DE] Germany .................. 195 41 919.7

[51] Int. Cl.$^6$ .................................................. A61K 37/12
[52] U.S. Cl. ................................................... 514/563
[58] Field of Search ........................................ 514/563

[56] References Cited

U.S. PATENT DOCUMENTS 5,304,574  4/1994  Leung ........................ 514/564
5,508,282  4/1996  Tulin-Silver et al. ........ 514/264

*Primary Examiner*—Keith D. MacMillan
*Attorney, Agent, or Firm*—Vorys Sater Seymour & Pease LLP

[57] ABSTRACT

A pharmaceutical preparation for the treatment of acute rhinitis contains, in combination and in physiological concentration, a) a sympathomimetic having a 2-imidazoline structure which is suitable for topical use or its physiologically acceptable salts; and b) a pantothenic functional compounds which is b1) pantothenol or its derivatives, in particular esters; and/or b2) pantothenic acid or its physiologically acceptable salts.

28 Claims, No Drawings

PHARMACEUTICAL COMPOSITION FOR TREATING ACUTE RHINITIS

BACKGROUND OF THE INVENTION

1. Field of the Invention

The present invention relates to a pharmaceutical preparation for treating acute rhinitis.

2. Brief Description of the Prior Art

There are a plurality of alpha-sympathomimetics available for the treatment of acute rhinitis, which on account of their vasoconstrictory properties lead to detumescence of the nasal mucous membrane after local administration to the nose. On repeated use of these substances, however, a dehydration with inflammatory irritation of the nasal mucous membranes is often experienced. This situation not infrequently leads to an increased danger of infection, as the mucous membranes in the dehydrated and inflamed condition can no longer fully maintain their protective and filter functions and thus the pathogenic organisms can reach the airways unhindered.

SUMMARY OF THE INVENTION

The present invention has as its object to provide a pharmaceutical preparation for treating acute rhinitis, which avoids the disadvantages of already-known preparations, in particular dehydration and inflammatory irritations of the nasal mucous membranes.

This object is achieved according to the invention by a pharmaceutical preparation which comprises in combination and in physiological concentration
a) a sympathomimetic containing a 2-imidazoline structure, which is suitable for topical use, or its physiologically acceptable salts, and
b) a pantothenic-functional compound which is
  b1) pantothenol or its derivatives, in particular esters and/or
  b2) pantothenic acid or its physiologically acceptable salts.

As the pantothenic-functional component, dexpanthenol (D(+)-pantothenyl alcohol, D(+)-pantothenol) is preferred.

DETAILED DESCRIPTION OF THE INVENTION AND PREFERRED EMBODIMENTS

The anti-inflammatory effect of dexpanthenol and its ability to potentiate defense against infections are known (see, for example Weber, Deutsche Apotheker Zeitung 123, 1921 (1983)). Dexpanthenol is also already commercially available in the form of a nasal ointment (Rote Liste 1995).

However, it could not have been predicted that a pharmaceutical preparation which contains pantothenol or pantothenic acid in combination with α-sympathomimetics having a 2-imidazoline structure would be very much better suited for the treatment of acute rhinitis than the known single-ingredient preparations and, as a result of a synergistic effect, would avoid dessication and inflammatory irritations of the nasal mucous membranes during use.

Sympathomimetics of the 2-imidazoline structure are characterized by a molecular structure which incorporates an imidazoline ring having a substituent, typically an aromatic or substituted aromatic group in the 2-position. Such compounds are well-known to those skilled in the art, and those suitable for topical use include those known by the pharmaceutical generic names oxymetazoline, xylometazoline, tramazoline, tetryzoline (tetrahydrozoline) and naphazoline and their pharmaceutically acceptable salts (see Erhart-Ruschig, Arzneimittel (Medicaments) Volume 2, Therapeutika mit Wirkung auf das periphere Nervensystem (Therapeutics having action on the Peripheral Nervous System), p. 150, Table 6). Such salts typically include the hydrochloride salts and the like.

The combination preparation according to the invention contains a pantothenic-functional compound, i.e., a compound having pantothenic acid activity, such as pantothenol or derivatives thereof of equivalent function, e.g., esters thereof, or pantothenic acid or its physiologically acceptable salts, preferably in amounts from 0.2 to 10% by weight, in particular 0.2 to 5% by weight.

The sympathomimetic can be present in amounts from 0.01 to 0.1% by weight, preferably 0.01 to 0.05% by weight. In particular, it is preferably present in the concentration 0.05% by weight for adults and 0.025% by weight for children.

The preparation according to the invention contains the components a) and b) (which may be b1) and/or b2)) preferably in a ratio from 1:50 to 1:500 by weight.

The pharmaceutical preparations can be liquid or viscous to semisolid. They can be, for example, ointments, creams or gels for introducing into the nose or as solutions for administration dropwise or by spraying.

Suitable excipients for liquid dosage forms are, in particular, aqueous systems with or without addition of glycerol, sorbitol and other polyols. Suitable excipients for viscous or semisolid pharmaceutical preparations, such as, for example, ointments, creams or gels, are, for example, paraffin hydrocarbons, petroleum jelly, wool wax products and other pharmaceutically acceptable, viscosity-increasing base materials. Hydrophilic gels may comprise, for example, water, glycerol or sorbitol, gelled using appropriate swelling substances such as, for example, polyacrylic acid, cellulose derivatives, starch or gum tragacanth.

Besides the active and excipient substances and optional emulsifiers present, the pharmaceutical preparations can additionally contain other auxiliary ingredients and/or additives which are pharmaceutically acceptable and compatible with the active compounds, such as, for example, fillers, extenders, binders, wetting agents, stabilizers, colorants, buffers and aromatic substances. Furthermore, microbiologically active chemical compounds such as, for example, preservatives or antiseptics, can be included in the preparations in the pharmaceutically customary concentrations to improve the microbial stability.

Moreover, the preparations according to the invention can also additionally contain one or more other pharmacologically active substances. In particular, additional compounds having pantothenic acid activity can be incorporated in free form and/or in the form of derivatives.

The preparations according to the invention are prepared by mixing or dissolving the active substances, at the pharmacologically active concentration, the auxiliary ingredients and/or additives and, if appropriate, the additional pharmacologically active substances in the selected excipient medium.

To demonstrate the synergistic effect of the preparations according to the invention, clinical experiments were conducted in which one nasal cavity of each patient was treated with xylometazoline hydrochloride or oxymetazoline hydrochloride solution alone and the opposite nasal cavity was treated with a preparation according to the invention in the form of an aqueous solution of xylometazoline hydrochloride or oxymetazoline hydrochloride and dexpanthenol.

In this series of experiments, continuous rhinoscopy of the nasal cavities treated with the preparation according to the invention showed a distinct clinical improvement compared with the sympathomimetics alone. Moreover, it was observed that when using the preparation according to the invention, in comparison with xylometazoline hydrochloride or oxymetazoline hydrochloride alone, there was no detectable irritant action and dessication of the mucous membrane.

When using the preparations according to the invention, no serious side effects should be expected based on the scientific knowledge existing to date about the individual active compounds. In the experiments summarized above likewise no side effects could be observed.

In reports of the university clinic and out-patients' department for ear, nose and throat diseases at the University Hospital of Hamburg-Eppendorf, which are described below in the examples, the synergistic effect achieved by combination preparations according to the invention was confirmed in clinical experiments in which the preparations were administered to patients with rhinitis.

The following working examples illustrate the preparation of liquid and semisolid preparations according to the invention, but are not to be considered as restrictive. The practitioner of ordinary skill in the art can see with the aid of the examples how, by variation of the individual parameters, the preparations according to the invention are to be adapted to the particular conditions without, however, departing from the invention.

EXAMPLE 1

To prepare 100 g of a clear aqueous solution for adults, 5 g of dexpanthenol and 90 g of purified water are introduced into a glass vessel equipped with a stirrer and the substance is completely dissolved by thorough stirring. A quantity of 0.02 g of benzalkonium chloride is added to the solution as a preservative and likewise dissolved with stirring. A quantity of 0.05 g of oxymetazoline hydrochloride is then added, and the solution is made up with additional water to a final weight of 100.0 g and stirred until homogeneous. If necessary, the solution is filtered through neutral cellulose filters, then filled into narrow-necked brown glass bottles of 10 or 20 ml, which can be provided with either a medicine dropper or a metered spray pump.

Procedure for use: Administer one drop or spray into each nostril 2 to 3 times daily and aspirate.

EXAMPLE 2

To prepare 100 g of a clear aqueous solution for children, 5 g of dexpanthenol and 90 g of purified water are introduced into a glass vessel equipped with a stirrer and the substance is completely dissolved by thorough stirring. A quantity of 0.02 g of benzalkonium chloride is added to the solution as a preservative and likewise dissolved with stirring. A quantity of 0.025 g of oxymetazoline hydrochloride is then added, and the solution is made up with additional water to a final weight of 100.0 g and stirred until homogeneous. If necessary, the solution is filtered through neutral cellulose filters, then filled into narrow-necked brown glass bottles of 10 or 20 ml, which can be provided with either a medicine dropper or a metered spray pump.

Procedure for use: Administer one drop or spray to each nostril 2 to 3 times daily and aspirate.

EXAMPLE 3

To prepare 100 g of a clear, buffered aqueous solution having a potentiated pantothenic acid action, 7.5 g of dexpanthenol are introduced into a glass vessel equipped with a stirrer along with 85 g of purified water and completely dissolved by thorough stirring. To adjust to a stable pH of 5.3, 0.756 g of potassium dihydrogen phosphate and 0.024 g of sodium monohydrogen phosphate dodecahydrate are added as buffers and, as a preservative, 0.02 g of benzalkonium chloride is added to the solution and the added materials are dissolved with stirring. The solution is mixed with 0.05 g of oxymetazoline hydrochloride, made up to a final weight of 100.0 g with additional water and stirred until homogeneous. If necessary, the solution is filtered through neutral cellulose filters. The clear, odorless liquid is filled into narrow-necked brown glass bottles of 10 or 20 ml, which can be provided with either a medicine dropper or a metered spray pump.

Procedure for use: Administer one drop or spray 2 to 3 times daily to each nostril and aspirate.

EXAMPLE 4

To prepare 100 g of a clear, buffered aqueous solution having increased adherence to tissue, 5 g of dexpanthenol and 0.02 g of benzalkonium chloride as preservative are introduced into a glass vessel equipped with a stirrer along with 80 g of purified water and completely dissolved by stirring. To adjust to a stable pH of 5.3, 0.756 g of potassium dihydrogen phosphate and 0.024 g of sodium monohydrogen phosphate dodecahydrate are added to the solution and dissolved with stirring. To reduce the surface tension and increase the viscosity, 0.5 g of 70% sorbitol solution and 0.5 g of 85% glycerol are added to the solution and the mixture is mixed with 0.05 g of oxymetazoline hydrochloride and made up with additional water to a final weight of 100.0 g. Finally, the solution is stirred until it is free from visible striations and homogeneous and filtered if necessary through neutral cellulose filters. The clear, odorless liquid is filled into narrow-necked brown glass bottles of 10 or 20 ml, which can be provided with either a medicine dropper or a metered spray pump.

Procedure for use: Administer one drop or spray 2 to 3 times daily to each nostril and aspirate.

EXAMPLE 5

To prepare 100 g of a solution according to Example 3, but having potentiated pantothenic acid action, 10 g of dexpanthenol and 0.02 g of benzalkonium chloride as preservative are introduced into a glass vessel equipped with a stirrer together with 75 g of purified water and completely dissolved by thorough stirring. To reduce the surface tension and increase the viscosity and tissue adherence, 0.5 g of sorbitol solution and 0.5 g of 85% glycerol are additionally added to the solution and the mixture is mixed with 0.05 g of oxymetazoline hydrochloride and made up with additional water to a final weight of 100.0 g. It is then stirred until it is free from visible striations and homogeneous and filtered if necessary through neutral cellulose filters. The clear, odorless liquid is filled into narrow-necked brown glass bottles of 10 or 20 ml, which can be provided with a medicine dropper or a metered spray pump.

Procedure for use: Administer one drop or spray 2 to 3 times daily to each nostril and aspirate.

EXAMPLE 6

To prepare 100 g of a viscous gel, a quantity of 0.625 g of polyacrylic acid is allowed to swell in 50 g of purified water in a covered glass vessel to give a sol. After about 24 hours, 0.1 g of 10% ammonia solution are introduced with intensive stirring, to initiate gel formation. Then in a second glass vessel, 5 g of dexpanthenol and 0.02 g of benzalkonium chloride as preservative are dissolved in 40 g of purified water and the clear solution is in turn slowly introduced into the polyacrylate gel with intensive stirring. Finally, the preparation is mixed with 0.05 g of oxymetazoline hydrochloride and made up with additional water to a final weight of 100.0 g and the product is stirred until it is homogeneous. An almost clear, colorless and odorless viscous gel is obtained, which is filled into small tubes of 5 or 10 g having an extended application tip.

Procedure for use: As required, 2 to 3 times daily, introduce a small portion of gel as high as possible into both nostrils and aspirate.

EXAMPLE 7

To prepare a creamy nasal ointment for children, 0.025 g of oxymetazoline hydrochloride and 5 g of dexpanthenol and, for preservation, 0.02 g of benzalkonium chloride are dissolved in sufficient purified water to make 30.0 g of solution in a glass vessel using a stirring rod. In an ointment mortar with a pestle, the aqueous active compound solution is incorporated into 70 g of wool wax alcohol ointment and finely emulsified with vigorous stirring. A white, soft nasal ointment is obtained, which is filled into small tubes of 5 or 10 g with an extended application tip.

Procedure for use: Two or three times daily administer a small portion of ointment to each nostril and, after it softens due to body warmth, aspirate.

EXAMPLE 8

This example illustrates the treatment of rhinitis with a combination of oxymetazoline and dexpanthenol Oxymetazoline is a member of the α-sympathomimetics group of drugs, which, by reason of their vasoconstrictory properties are extensively used in therapy by topical administration to swollen nasal mucous membranes in the course of the treatment of rhinitis. As a result of a "rebound effect" after repeated use of oxyometazoline, a medicament-related rhinitis with inflammatory irritation of the nasal mucous membranes can occur. Consequently, the opportunities for the therapeutic use of oxymetazoline have been severely limited. However, it has been unexpectedly discovered that when dexpanthenol in combination with oxymetazoline is topically applied to the nasal mucous membranes a curative response is clinically apparent even after a relatively short period of treatment.
Procedure:

Ten patients afflicted with rhinitis were treated both with oxymetazoline nasal spray (0.05%) and with the combination of dexpanthenol-oxymetazoline nasal spray (5.0% +0.05%) by the procedure described above. Based on the improvement in the symptomatology of nasal swelling, it was clearly possible to show the vasoconstrictory effect of oxymetazoline in all patients. It was striking and surprising to observe that the irritation associated with oxymetazoline did not occur after administration of the combination, which resulted in greater patient compliance. The nasal detumescent effect after treatment with the combination manifested itself as clinically significantly more prominent than expected. This was corroborated in that the clinical effect after treatment with the combination lasted longer, and at the same time a clearly superior result was achieved. On account of these therapeutic test results, the therapy with the single substance was usually terminated after 3 days' to 7 days' therapy in order to be continued using the combination with its clearly better clinical effect.
Conclusion:

The results of the therapeutic test indicate synergism of the activities of the vasoconstrictor oxymetazoline and dexpanthenol, which produces a clinically impressive improvement in the treatment of rhinitis that clearly surpasses the level attained by the individual active compounds.

EXAMPLE 9

This example illustrates treatment of rhinitis with a combination of xylometazoline and dexpanthenol Xylometazoline is a member of the α-sympathomimetic group of drugs, which because of their vasoconstrictory properties are extensively used in therapy by topical administration to swollen nasal mucous membranes in the course of the treatment of rhinitis. As a result of a "rebound effect" after repeated use of xylometazoline, a medicament-related rhinitis with inflammatory irritation of the nasal mucous membranes can occur as a result of which opportunities for the therapeutic use of xylometazoline have been severely limited.

However, it has been unexpectedly discovered that when dexpanthenol in combination with xylometazoline is topically applied to the nasal mucous membranes, even after a rather brief treatment period, a more distinct curative response is clinically apparent than after treatment with xylometazoline alone.
Procedure:

In the course of the therapy of rhinitis, 12 patients were each treated with a xylometazoline nasal spray (0.05%) and also a combination of dexpanthenol (5%) with xylometazoline (0.05%) by the procedure described above. In all patients, it was possible to show a clear improvement in nasal swelling, corresponding to the mechanism of action of the vasoconstrictory effect of xylometazoline.

It was striking and surprising to observe that the irritation associated with xylometazoline did not occur after administration of the combination, which resulted in greater patient compliance. The nasal detumescent effect after treatment with the combination manifested itself as clinically significantly more prominent as compared to treatment with xylometazoline alone. This unexpected clinical effect was corroborated in that the activity after treatment with the combination lasted longer, and at the same time a better healing result was achieved. On account of these therapeutic test results, treatment with xylometazoline on its own was usually terminated after 3 to 7 days' therapy in order to be continued with the combination of xylometazoline and dexpanthenol with a clearly better clinical effect.
Conclusion:

The clinical investigations confirm an unexpected synergism of the activities of xylometazoline and dexpanthenol which leads to a clinically more evident improvement in the treatment of rhinitis, that clearly surpasses the capabilities of the individual active compounds.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

We claim:

1. A pharmaceutical preparation for the topical treatment of acute rhinitis, comprising, in pharmaceutically effective amounts,
   a) a sympathomimetic having a 2-imidazoline structure which is suitable for topical use or its physiologically acceptable salts; and
   b) a pantothenic-functional compound selected from the group consisting of
      b1) pantothenol or its physiologically equivalent derivatives, in particular esters; and
      b2) pantothenic acid or its physiologically acceptable salts.

2. A pharmaceutical preparation as claimed in claim 1, wherein said sympathomimetic is selected from the group consisting of oxymetazoline, xylometazoline, tramazoline, tetryzoline and naphazoline and their pharmaceutically acceptable salts.

3. A pharmaceutical preparation as claimed in claim 1, wherein the sympathomimetic is oxymetazoline hydrochloride.

4. A pharmaceutical preparation as claimed in claim 1, wherein the sympathomimetic is xylometazoline hydrochloride.

5. A pharmaceutical preparation as claimed in claim 1, wherein said pantothenic-functional compound is D(+)-pantothenol.

6. A pharmaceutical preparation as claimed in claim 1, wherein the sympathomimetic is selected from the group consisting of oxymetazoline hydrochloride and xylometazoline hydrochloride, and said pantothenic-functional compound is D(+)-pantothenol.

7. A pharmaceutical preparation as claimed in claim 1, containing the sympathomimetic a) in amounts from 0.01 to 0.1% by weight.

8. A pharmaceutical preparation as claimed in claim 7, containing the sympathomimetic a) in amounts from 0.01 to 0.05% by weight.

9. A pharmaceutical preparation as claimed in claim 1, containing component b) in amounts from 0.2 to 10% by weight.

10. A pharmaceutical preparation as claimed in claim 9, containing component b) in amounts from 0.2 to 5% by weight.

11. A pharmaceutical preparation as claimed in claim 1, containing the sympathomimetic a) in amounts from 0.01 to 0.1% by weight and component b) in amounts from 0.2 to 10% by weight.

12. A pharmaceutical preparation as claimed in claim 10, containing the sympathomimetic a) in amounts from 0.01 to 0.05% by weight and component b) in amounts from 0.2 to 5% by weight.

13. A pharmaceutical preparation as claimed in claim 1, containing the components a) and b) in a ratio of from 1:50 to 1:500.

14. A pharmaceutical preparation as claimed in claim 1, additionally comprising one or more auxiliary ingredients selected from the group consisting of fillers, extenders, binders, wetting agents, stabilizers, colorants, buffers, aromatic substances, preservatives, and antiseptics.

15. A method of treating acute rhinitis comprising administering to inflamed nasal mucous membranes a pharmaceutically effective amount of a pharmaceutical preparation, comprising, in pharmaceutically effective amounts,
   a) a sympathomimetic having a 2-imidazoline structure which is suitable for topical use or its physiologically acceptable salts; and
   b) a pantothenic-functional compound selected from the group consisting of
      b1) pantothenol or its physiologically equivalent derivatives, in particular esters; and
      b2) pantothenic acid or its physiologically acceptable salts.

16. The method of claim 15, wherein said sympathomimetic is selected from the group consisting of oxymetazoline, xylometazoline, tramazoline, tetryzoline and naphazoline and their pharmaceutically acceptable salts.

17. The method of claim 15, wherein the sympathomimetic is oxymetazoline hydrochloride.

18. The method of claim 15, wherein the sympathomimetic is xylometazoline hydrochloride.

19. The method of claim 15, wherein said pantothenic-functional compound is D(+)-pantothenol.

20. The method of claim 15, wherein the sympathomimetic is selected from the group consisting of oxymetazoline hydrochloride and xylometazoline hydrochloride, and said pantothenic-functional compound is D(+)-pantothenol (dexpanthenol).

21. The method of claim 15, wherein said pharmaceutical preparation contains the sympathomimetic a) in amounts from 0.01 to 0.1% by weight.

22. The method of claim 21, wherein said pharmaceutical preparation contains the sympathomimetic a) in amounts from 0.01 to 0.05% by weight.

23. The method of claim 15, wherein said pharmaceutical preparation contains component b) in amounts from 0.2 to 10% by weight.

24. The method of claim 23, wherein said pharmaceutical preparation contains component b) in amounts from 0.2 to 5% by weight.

25. The method of claim 15, wherein said pharmaceutical preparation contains the sympathomimetic a) in amounts from 0.01 to 0.1% by weight and component b) in amounts from 0.2 to 10% by weight.

26. The method of claim 25, wherein said pharmaceutical preparation contains the sympathomimetic a) in amounts from 0.01 to 0.05% by weight and component b) in amounts from 0.2 to 5% by weight.

27. The method of claim 21, wherein said pharmaceutical preparation contains the components a) and b) in a ratio of from 1:50 to 1:500 by weight.

28. The method of claim 21, wherein said pharmaceutical preparation additionally comprises one or more auxiliary ingredients selected from the group consisting of fillers, extenders, binders, wetting agents, stabilizers, colorants, buffers, aromatic substances, preservatives, and antiseptics customary excipients and additives.

* * * * *